US00PP10654P

United States Patent [19]

Egger

[11] Patent Number: Plant 10,654

[45] Date of Patent: Oct. 20, 1998

[54] ASIATIC HYBRID LILY PLANT NAMED 'HELIOS'

[75] Inventor: Donald L. Egger, Wilsonville, Oreg.

[73] Assignee: Cebeco Lilies, Inc., Aurora, Oreg.

[21] Appl. No.: 788,112

[22] Filed: Jan. 23, 1997

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 5,994 5/1987 McRae ..... Plt./87.4

P.P. 7,919 7/1992 Veenstra ..... Plt./87.4

P.P. 8,365 9/1993 Vletter ..... Plt./87.4

*Primary Examiner*—James R. Feyrer

*Assistant Examiner*—Kent L. Bell

*Attorney, Agent, or Firm*—Klarquist Sparkman Campbell Leigh & Whinston

[57] ABSTRACT

A new and distinct upright Asiatic lily hybrid named 'Helios' having numerous, large bright yellow flowers, large yellow buds, high bud count, and strong stems with good foliage quality excellent for cut flowers.

1 Drawing Sheet

BACKGROUND OF THE INVENTION

The present invention relates to a new and distinct cultivar flowering of lily hybrid referred to commercially as an upright Asiatic hybrid lily and given the cultivar name 'Helios'.

This invention was developed by controlled breeding in Aurora, Oreg. using A-080-78, a proprietary, non-released plant as the seed parent and A-034-84, another proprietary, non-released plant as the pollen parent.

This invention has not been observed under all possible environmental conditions. The phenotype may vary significantly with variations in environment such as temperature, light intensity and day length, without however, any variation in genotype.

The following traits have been repeatedly observed and are determined to be the basic characteristics of this invention which in combination distinguish this lily as a new and distinct cultivar: (1) large, bright, clear yellow flowers with no spots; (2) large, yellow buds; (3) high bud count; (4) long lasting flowers; (5) strong stems with good quality foliage; (6) good vase life; and (7) early flowering. Bulbs of this plant may be precooled and forced out of season for uniform cut flower production. In addition, this new lily shows good disease and virus resistance.

Compared to 'London,' this invention has no spots, better yellow color, better substance, stronger stems, and better bud color.

Asexual reproduction of this new variety has been accomplished at Cebeco Lilies, Inc., Aurora, Oreg. by scaling and tissue culture. The resulting plants have shown that the abovementioned unique features are stable and reproduce true to type in each successive propagation.

Figure 1:
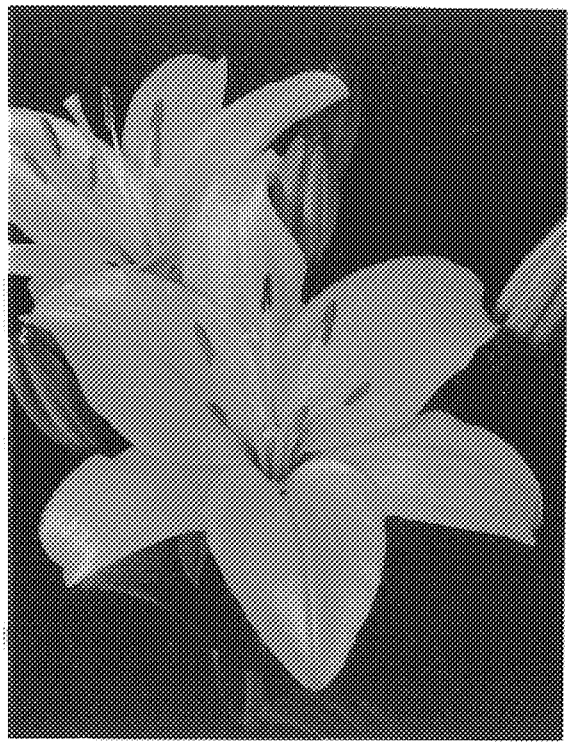
FIG. 1 is a close-up photograph which illustrates in greater detail a single flower of the new plant.
Figure 2:
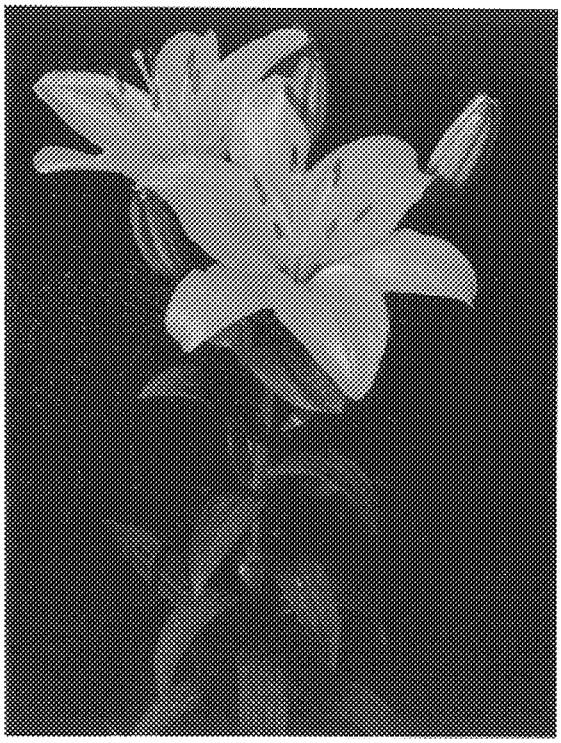
FIG. 2 is a photograph showing the 'Helios' lily.

The photographs of the drawing were taken in Jun. 1995 in a studio and illustrate the typical flower and foliage form, with color as true as reasonably possible in this type of the color photograph.

DETAILED DESCRIPTION

The following is a detailed description of the invention based on plants produced under commercial practices in the Cebeco Lilies, Inc. greenhouse in Aurora, Oreg. in Jun. 1995. Color references are made to The Royal Horticultural Society Colour Chart, except where the context indicates a term having its ordinary dictionary meaning.

The Plant

Origin: Seedling.

Parentage:

*Seed parent*.—A-080-78.

*Pollen parent*.—A-034-84.

Commercial classification: Hybrid Asiatic Lily, cut flower type.

Classification: Division I-A, Upright Asiatic Hybrid Lily, according to the Horticultural Classification of Lilies by the Royal Horticultural Society of London.

Form: Single erect, thick stem bearing terminal cluster of flowers.

Height: About 86 cm. from the top of the soil to the top of the flowers from bulbs of 12–14 cm. in circumference.

Stem color: Yellow green (144A).

Growth habit: Vigorous, upright and rigid.

Internodes: About 2–12 mm.

Foliage:

*Arrangement*.—Spiral.

*Leaf size*.—To about 115 mm. long and 18 mm wide.

*Leaf shape*.—Lanceolate to broadly lanceolate near the inflorescence.

*Texture*.—Leathery, thick.

*Aspect*.—Glossy.

*Color*.—Medium green on both sides. Between yellow green Group 147A and 137A. Lighter underneath.

Bulbs:

*Size*.—Variable, ranging to about 12–14 cm. in circumference as used commercially.

*Color*.—White.

The Bud

Size: About 90 mm. long and 28 mm. wide just prior to opening.

Shape: Ovoid with an obtuse tip.
Rate of opening: The mature bud opens slowly in response to light.
Color: Yellow (Yellow Group 7B) with yellow green at apex.

The Flower

Blooming habit: Annually, once and early season.
Days to bloom: Flowers approximately 74 days after spring greenhouse planting under typical commercial flower forcing conditions of 15 degrees Celsius night time temperatures.
Inflorescence size: About 22 cm. high and 28 cm. wide when there are five flowers present.
Flower size: Large.
*Diameter*.—About 15 cm.
*Depth*.—About 5 cm.
Borne: In an umbel-like raceme when there are 4 or fewer flowers and the pedicels branch when there are 5 or more flowers.
Shape: When the flower first opens it is a V-shaped bowl. Later the shape flattens out slightly and the tepals reflex slightly at the tips.
Tepalage:
*Number*.—Six.
*Arrangement*.—Imbricated.
*Shape*.—Ovate.
*Texture*.—Spongy, waxy.
*Aspect*.—Satiny.
*Size*.—Length: About 100 mm. Width: Inner tepals — about 48 mm. Outer tepals — about 35 mm. Depth of imbrication: About 10 mm.
*Nectary*.—About 22 mm. long; yellow green (144B); channels together.
*Projections*.—Few, as rough areas close to the nectary.
*Spots*.—None.
*Blush*.—None.
*Color*.—Topside: Yellow. Yellow Group 9A. Bottomside: Yellow Group 9A at the edges to Yellow 8B around the midrib.
*Discoloration*.—None.
*Fragrance*.—None.
Pedicle:
*Length*.—About 6–14 cm.
*Color*.—Yellow green 144A.
*Orientation*.—Ascending upwardly in a curve varying from 20°–60° from the horizontal.

The Reproductive Organs

Stamens:
*Number*.—Six, typical of the genus Lilium.
*Anthers before dehiscence*.—Size: About 20 mm. Color: Greyed Orange 166D.
*Filaments*.—Length: About 69 mm. Color: Yellow Group 8B on top half to lighter at base.
*Pollen*.—Color: Orange. Orange Group 26A.
Pistil:
*Number*.—One.
*Style*.—Length: About 60 mm. Color: Yellow Group 9B-C.
*Stigma*.—Color: Yellow Group 9B with faint Greyed Orange 176A as dots over receptive surface.

The Fruit

Fertility: Fertile.
Shape: Ovoid.
Color at maturity: Soft Brown.

I claim:

1. A new and distinct cultivar of Asiatic hybrid lily plant substantially as herein shown and described.

* * * * *